United States Patent
Yuan

(10) Patent No.: US 8,789,231 B2
(45) Date of Patent: Jul. 29, 2014

(54) TEXTURED COTTON WIPES

(75) Inventor: James Yuan, Westport, CT (US)

(73) Assignee: Xamax Industries, Inc., Seymour, CT (US)

( * ) Notice: Subject to any disclaimer, the term of this patent is extended or adjusted under 35 U.S.C. 154(b) by 0 days.

(21) Appl. No.: 13/158,065

(22) Filed: Jun. 10, 2011

(65) Prior Publication Data

US 2011/0302733 A1   Dec. 15, 2011

Related U.S. Application Data

(60) Provisional application No. 61/397,360, filed on Jun. 10, 2010.

(51) Int. Cl.
| | |
|---|---|
| A47K 7/00 | (2006.01) |
| A47L 13/16 | (2006.01) |
| A47L 13/17 | (2006.01) |
| A61Q 19/00 | (2006.01) |
| A47K 7/03 | (2006.01) |
| A61K 8/02 | (2006.01) |
| A45D 34/04 | (2006.01) |

(52) U.S. Cl.
CPC . *A47K 7/03* (2013.01); *A61Q 19/00* (2013.01); A45D 2200/1054 (2013.01); A61K 2800/10 (2013.01); *A61K 8/0208* (2013.01); *A45D 34/04* (2013.01)
USPC .......................... 15/104.93; 15/208; 15/209.1

(58) Field of Classification Search
USPC ................................ 15/104.93, 209.1, 229.11
IPC ................ A47K 7/00; A47L 25/00; B08B 1/00
See application file for complete search history.

(56) References Cited

U.S. PATENT DOCUMENTS

| | | | |
|---|---|---|---|
| 6,737,114 B2 | 5/2004 | Dawson, Jr. et al. | |
| 7,105,716 B2 * | 9/2006 | Baratian et al. | 604/367 |
| 7,127,771 B2 * | 10/2006 | McDevitt et al. | 15/227 |
| 2006/0141014 A1 | 6/2006 | Eknoian et al. | |
| 2007/0283516 A1 | 12/2007 | Rasmussen et al. | |
| 2008/0075748 A1 | 3/2008 | Hasenoehrl et al. | |

FOREIGN PATENT DOCUMENTS

| | | | |
|---|---|---|---|
| WO | 03103626 | 12/2003 | |
| WO | WO 2007122594 | * 11/2007 | A47L 13/18 |
| WO | WO2007122594 | * 11/2007 | A47L 13/18 |

OTHER PUBLICATIONS

International Search Report for PCT/US11/40016, Aug. 29, 2011.

* cited by examiner

*Primary Examiner* — Monica Carter
*Assistant Examiner* — Stephanie Berry
(74) *Attorney, Agent, or Firm* — Baker & McKenzie LLP

(57) ABSTRACT

A textured wipe is provided that includes a non-woven or woven cotton wipe sheet, and in some embodiments a plurality of beads and/or a coating. The cotton wipe sheet has a wipe surface and an opposing back surface. The plurality of beads is adhered to the wipe surface. Each bead is formed to have a three dimensional geometry that extends outwardly from the wipe surface.

23 Claims, 1 Drawing Sheet

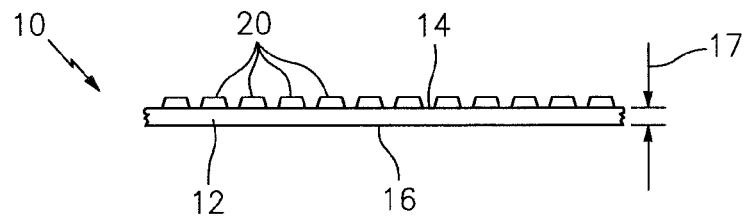
*FIG. 1*
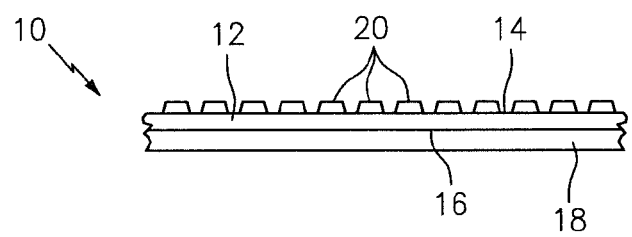
*FIG. 2*
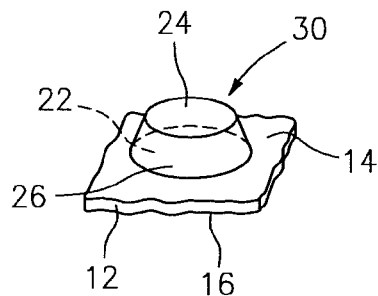 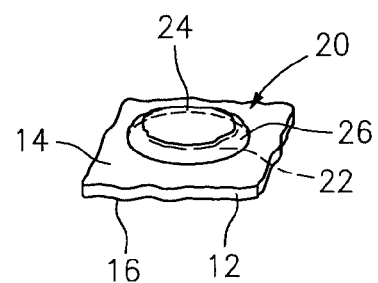
*FIG. 3*   *FIG. 4*
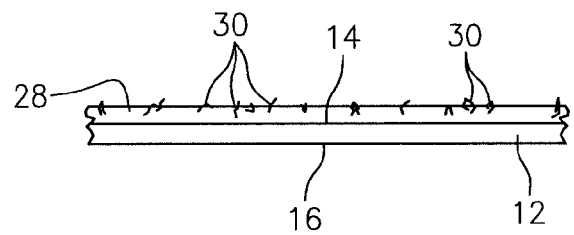
*FIG. 5*
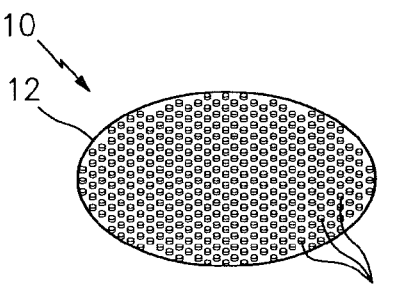 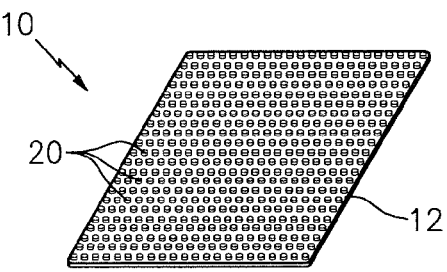
*FIG. 6*   *FIG. 7*

TEXTURED COTTON WIPES

Applicant hereby claims priority benefits under 35 U.S.C. §119(e) of U.S. Provisional Patent Application No. 61/397,360 filed Jun. 10, 2010, the disclosure of which is herein incorporated by reference.

BACKGROUND OF THE INVENTION

1. Technical Field

This invention relates to a non-woven or woven fabric containing cotton and whose properties are enhanced by coated or saturated substances; to the method of forming this material; to components that are surfaced and/or saturated by this material; and to the method of forming those components. More particularly, this invention relates to a non-woven or woven fabric pad containing cotton and in some embodiments also containing, soap (wet or dry) liquids or creams for: human skin cleansing and/or exfoliation; cleaning of surfaces. The invention preferably takes the form of hand held pads and/or cloth wherein the material produces mild surface abrasion and pleasing stimulating tactile sensation to the skin of the user.

2. Background Information

The current standard non-woven and woven substrate materials that are enhanced by coated substances that are designed for cleansing and exfoliating human skin typically are made of thermoplastic non-cotton materials. Disposable wipes for human skin that are made of mostly thermoplastic substrates are not typically biodegradable and will not decompose in an eco-friendly manner. Current one hundred percent (100%) cotton wipe materials on the market, claimed as textured or exfoliating, involve using cotton that is a hydro entangled non-woven with apertures (small holes) that give the impression of exfoliating.

It would be desirable to have a cleansing and/or exfoliating or cleaning material that overcomes the above short comings of the presently used mostly thermoplastic substrate human skin wipes.

SUMMARY OF THE INVENTION

According to an aspect of the invention, a textured wipe is provided that includes a non-woven or woven cotton wipe sheet and a plurality of beads. The cotton wipe sheet has a wipe surface and an opposing back surface. The plurality of beads is adhered to the wipe surface. Each bead is formed to have a three dimensional geometry that extends outwardly from the wipe surface.

According to another aspect of the invention, a textured wipe is provided that includes a non-woven or woven cotton wipe sheet and a plurality of beads. The cotton wipe sheet has a wipe surface and an opposing back surface. The plurality of beads is adhered to the wipe surface. Each bead includes a puffing agent, and each bead is formed to have a three dimensional geometry that extends outwardly from the wipe surface.

According to another aspect of the present invention, a textured wipe is provided that includes a non-woven or woven cotton wipe sheet and a plurality of beads. The cotton wipe sheet has a wipe surface and an opposing back surface. The plurality of beads is adhered to the wipe surface. Each bead comprises a thermoplastic material, and each bead is formed to have a three dimensional geometry that extends outwardly from the wipe surface.

According to another aspect of the present invention, a textured wipe is provided that includes a non-woven or woven cotton wipe sheet and a coating. The cotton wipe sheet has a wipe surface and an opposing back surface. The coating includes an acrylic binder and/or abrasive particles.

The textured wipes of this invention may be used as a bath facecloth, a makeup remover, an exfoliating wipe, a surface cleaner, or as a cleaning wipe for general purposes. Cotton is completely biodegradable, and provides an ecosystem-friendly wipe pad and/or cleaning pad.

The present textured wipe and advantages associated therewith will become more readily apparent in view of the detailed description provided below, including the accompanying drawings.

BRIEF DESCRIPTION OF THE DRAWINGS

FIG. 1 is a diagrammatic cross-sectional view of a textured wipe embodiment according to the present invention.

FIG. 2 is a diagrammatic cross-sectional view of a textured wipe embodiment according to the present invention.

FIG. 3 is a diagrammatic perspective view of a bead embodiment, having a truncated conical shape.

FIG. 4 is a diagrammatic perspective view of a bead embodiment, having a partially spherical shape.

FIG. 5 is a diagrammatic cross-sectional view of a textured wipe embodiment according to the present invention, including a coating adhered to the wipe surface of the cotton wipe sheet.

FIG. 6 is a perspective view of an embodiment of the present textured wipe, having a circular geometry.

FIG. 7 is a perspective view of an embodiment of the present textured wipe having a rectangular geometry.

DETAILED DESCRIPTION OF THE INVENTION

Referring to FIGS. 1-7, a textured wipe 10 is provided that includes a non-woven or woven cotton wipe sheet 12. An example of a non-woven cotton wipe sheet 12 is formed from intertwined cotton fibers, and preferably the non-woven cotton wipe sheet 12 consists of one hundred percent (100%) intertwined cotton fibers. Spuntech Industries, Inc. of Roxboro, N.C. produces acceptable non-woven cottons.

The cotton wipe sheet 12 includes a wipe surface 14 and an opposing back surface 16. For those applications where the wipe 10 is designed to be used as a cleaning and/or exfoliating wipe for human skin, a sheet thickness 17 of approximately 0.15 inches (~0.38 mm) provides advantageous durability. The cotton wipe sheet 12 is not limited to this thickness 17, however. In some embodiments, the wipe sheet 12 includes a backer sheet 18 (see FIG. 2) that is fixed to the back surface 16 of the cotton wipe sheet 12. In those embodiments that include backer sheet 18, the backer sheet 18 may be attached to the periphery of the back surface 16 of the wipe sheet 12, thereby forming an internal pocket where the center region of the back surface 16 is not attached to the backer sheet 18. The backer sheet 18 may comprise the same material as the cotton wipe sheet 12 or it may be a different material.

In some embodiments (e.g., see FIGS. 1-4, 6, and 7) the textured wipe 10 further includes a plurality of beads 20 adhered to the wipe surface 14, and each bead 20 is formed to have a three dimensional geometry that extends outwardly from the wipe surface 14. The beads 20 are preferably formed into a three dimensional geometric configuration that includes a base surface 22, a contact surface 24, and at least one sidewall 26 extending between the base surface 22 and the contact surface 24. The base surface 22 of each bead 20 is contiguous with and adhered to the wipe surface 14. The base surface 22 has a surface area, and the contact surface 24 has a surface area, and the surface area of the base surface 22 is greater than the surface area of the contact surface 24. Examples of bead three-dimensional geometric configurations include a truncated conical shape (e.g., see FIG. 3) and a substantially hemispherical shape (e.g., see FIG. 4). These geometries are examples of bead geometric configurations, and the beads 20 are not limited thereto.

In a first embodiment, each bead 20 includes a puffing agent. Puffing agents are commercially available. An example of an acceptable commercially available puffing agent is Altoma Super Puff 406, from Bolger & O'Hearn, Inc. of Fall River, Mass., U.S.A. The composition that forms the bead 20 may also include an appropriate binding agent such as an acrylic emulsion that enhances the adherence of the composition, including the puffing agent, to the cotton wipe sheet 12. As will be described below, when a puff agent is exposed to an elevated temperature (e.g., elevated over ambient) it expands to at least in part create the three dimensional shapes of the beads 20.

In a second embodiment, the beads 20 comprise a thermoplastic material. Examples of acceptable thermoplastic plastics include, but are not limited to, one or more of polypropylene ("PP"), polyethylene ("PE"), acrylonitrile butadiene styrene ("ABS"), polyamide ("PA"; also referred to as "Nylon"), polyethylene terephthalate ("PET"), polyvinyl chloride ("PVC") or copolymers thereof. In this embodiment, the beads 20 may also include materials including abrasive particles and/or acrylic resin(s).

Now referring to FIG. 5, in some embodiments the textured wipe 10 includes a surface coating 28 that includes an acrylic binder. Acceptable acrylic binders include vinyl acrylic emulsions, acrylic emulsions, vinyl acrylic co-polymers, and vinyl acetate/ethylene emulsions. A specific example of acceptable acrylic binder is NACRYLIC 217 produced by Celanese Ltd., of Dallas, Tex., U.S.A. The present wipe is not limited to this specific acrylic binder, however. In some embodiments, the coating 28 further includes one or more of a skin cleaning agent, a medicinal agent, an exfoliating agent, and a soap material. An example of an acceptable exfoliating agent is abrasive particles 30 included in the coating that can provide a selectively abrasive surface. The specific type, size, and density of abrasive particles 30 within the coating 28 can be varied to suit the application at hand.

A variety of methods can be used to manufacture the present textured wipe 10. In those embodiments wherein the textured wipe 10 includes a plurality of beads 20 that include a puffing agent, the material that forms the beads 20 can be applied to the cotton wipe sheet 12 via an aqueous composition applied via a printing technique such as screen printing using a rotary screen printing machine. In this technique, the aqueous composition is forced through a specially prepared screen onto the cotton wipe sheet 12. The screen does not allow the passage of the aqueous composition through the screen except in defined openings. The positioning of the openings creates a predetermined pattern of the aqueous composition on the surface of the cotton wipe sheet 12. The particular pattern used can be varied to suit the application at hand; e.g., more or less beads 20, spacing between beads 20, etc. The size of the openings also is a factor in the amount of aqueous composition that passes through the openings, and therefore the size of the beads 20; e.g., all of the beads 20 may be of the same size, or certain beads 20 may be bigger or smaller than others, etc. After the aqueous composition is applied to the cotton wipe sheet 12, the sheet is subjected to a drying step at an elevated temperature (e.g., by microwave energy, infrared heating, steam, autoclaving, etc.), at which time the puffing agent forms a gas which causes the composition deposits to rise and create a three-dimensional shape on the substrate. As indicated above, in some instances, a binding agent may be added to the composition to enhance the adherence of the composition to the cotton wipe sheet 12. In some instances, the textured wipe 10 may be subsequently exposed to a second heat process for curing the deposited composition. Optimum drying and curing temperatures and durations can vary depending on the exact chemistry of the composition applied to the cotton wipe sheet 12.

In those embodiments wherein the textured wipe 10 includes a plurality of beads 20 that comprise a thermoplastic material, the material that forms the beads 20 can be applied to the cotton wipe sheet 12 via a die process wherein the thermoplastic material is extruded or otherwise forced through an applicator (e.g., a plate) having a plurality of holes arranged in a predetermined pattern. Like the screen described above, the positioning of the holes within the applicator and the pattern formed thereby can be varied to suit the application at hand; e.g., more or less beads 20, spacing between beads 20, etc. Also, the size of the openings can be varied to make the beads 20 all the same size, or make certain beads 20 bigger or smaller than others. After the bead 20 material is applied to the cotton wipe sheet 12, the sheet may be subjected to additional steps including one or more of a bead geometry forming step, a drying step, and a curing step, the latter operable to cure the thermoplastic material within the bead material. Also as indicated above, in some instances, a binding agent may be added to the bead material to enhance the adherence of the composition to the cotton wipe sheet 12. Optimum drying and curing temperatures and durations can vary depending on the exact chemistry of the bead material applied to the cotton wipe sheet 12.

In those embodiments wherein the textured wipe 10 includes a coating 28 adhered to the wipe surface 14 of the cotton wipe sheet 12, the coating 28 can be applied using conventional aqueous coating techniques that allow the aqueous solution to wet the cotton wipe sheet 12 and upon drying, adhere well to the fibers of the cotton wipe sheet 12. In these embodiments, the coating 28 may be applied to the entire wipe surface 14 or portions of the wipe surface 14; e.g., in a pattern. As indicated above, the coating 28 may also be used in combination with any of the textured wipe 10 embodiments that include a plurality of beads 20 applied to the wipe surface 14. For example, a coating 28 that includes one or more of a skin cleaning agent, a medicinal agent, an exfoliating agent, and a soap material can be applied to the wipe surface 14 after the beads 20 are applied. Alternatively, the beads 20 could be applied to the wipe sheet 12 and the coating 28 could be applied to the exposed surface of the backer sheet 18.

Referring to FIGS. 6 and 7, a particularly useful application of the present textured wipes 10 includes skin textured wipes 10 that each include the cotton wipe sheet 12 on which a plurality of beads 20 is adhered. For some specific applications, the wipes 10 are about two inches (~5.0 cm) wide and the cotton wipe sheet 12 is approximately 0.015 inches (~0.38 mm) thick. The height of the beads 20 is typically in the range of about 0.020-0.040 inches (0.051-0.102 mm), and the diameter of the beads 20 is typically in the range of about 0.040-0.60 inches (0.102-1.524 mm) at the base of the bead. In bead patterns that have uniformly separated beads, a bead to bead spacing in the range of 0.080-0.130 inches (0.203-0.330 mm) between bead centers is particularly useful. It will be appreciated that the aforesaid dimensions are only examples of the sizes of the wipe and its components, and should not be viewed as limiting the invention.

Although this invention has been shown and described with respect to the detailed embodiments thereof, it will be understood by those skilled in the art that various changes in form and detail may be made without departing from the spirit and scope of the invention. For example, in some embodiments, the beads and/or the coating can be applied to the backer sheet 18 to give the wipe two textured surfaces, including embodiments where the composition of the beads and/or coating is different on each side of the wipe.

What is claimed is:

1. A textured wipe pad, comprising:
   a cotton wipe sheet having a wipe surface and an opposing back surface;
   a plurality of beads adhered to the wipe surface, the beads having three dimensional geometry that extends outwardly from the wipe surface; and
   a backer sheet attached to the back surface of the cotton wipe sheet, wherein
   a width of the wipe pad is approximately two inches or less, and
   the beads include a puffing agent that forms a gas when exposed to an elevated temperature thereby causing the respective beads to rise and provide the three dimensional geometry.

2. The textured wipe pad of claim 1, wherein the backer sheet is attached to the back surface of the cotton wipe sheet around the periphery of the cotton wipe sheet, thereby forming an internal pocket where a central region of the back surface is not attached to the backer sheet.

3. The textured wipe pad of claim 1, wherein
   the beads respectively have a base surface contiguous with the wipe surface and adhered to the wipe surface, the base surface having a surface area, a contact surface having a surface area, and at least one side wall surface extending between the base surface and the contact surface, and
   the surface area of the base surface is greater than the surface area of the contact surface.

4. The textured wipe pad of claim 1, wherein the cotton wipe sheet includes non-woven or woven cotton.

5. The textured wipe pad of claim 1, wherein the beads include a plurality of solid beads.

6. The textured wipe pad of claim 1, wherein the beads have a truncated conical shape.

7. The textured wipe pad of claim 1, wherein the beads include abrasive particles.

8. The textured wipe pad of claim 1, further comprising a coating adhered to the wipe surface of the cotton wipe sheet, the coating including an acrylic binder.

9. The textured wipe pad of claim 8, wherein the coating includes one or more of a skin cleaning agent, a medicinal agent, an exfoliating agent, and a soap material.

10. The textured wipe pad of claim 9, wherein the exfoliating agent includes abrasive particles.

11. The textured wipe pad of claim 1, wherein at least one bead comprises a thermoplastic material.

12. The textured wipe pad of claim 11, wherein the thermoplastic material includes at least one of a thermoplastic polypropylene, polyethylene, acrylonitrile butadiene styrene, polyamide, polyethylene terephthalate, polyvinyl chloride, or copolymers thereof.

13. The textured wipe pad of claim 12, wherein the beads include an acrylic.

14. The textured wipe pad of claim 11, further comprising a coating adhered to the wipe surface of the cotton wipe sheet, the coating including an acrylic binder.

15. The textured wipe pad of claim 14, wherein the coating includes one or more of a skin cleaning agent, a medicinal agent, an exfoliating agent, and a soap material.

16. The textured wipe pad of claim 15, wherein the exfoliating agent includes abrasive particles.

17. The textured wipe pad of claim 1, wherein the backer sheet is made of a same material as the wipe sheet.

18. The textured wipe pad of claim 17, wherein
   a plurality of solid beads are adhered to an exterior surface of the backer sheet,
   the beads respectively have a base surface contiguous with the exterior surface and adhered to the exterior surface, the base surface having a surface area, a contact surface having a surface area, and at least one side wall surface extending between the base surface and the contact surface, and
   the surface area of the base surface is greater than the surface area of the contact surface.

19. The textured wipe pad of claim 18, wherein the beads respectively have a truncated conical shape.

20. The textured wipe pad of claim 18, further comprising a coating adhered to one or both of the wipe surface and the backer sheet, the coating including an acrylic binder and one or more of a skin cleaning agent, a medicinal agent, an exfoliating agent, and a soap material.

21. The textured wipe pad of claim 1, wherein
   a plurality of solid beads are adhered to an exterior surface of the backer sheet,
   the beads respectively having a base surface contiguous with the exterior surface and adhered to the exterior surface, the base surface having a surface area, a contact surface having a surface area, and at least one side wall surface extending between the base surface and the contact surface, and
   the surface area of the base surface is greater than the surface area of the contact surface.

22. The textured wipe pad of claim 1, wherein the plurality of beads respectively have heights in the range of about 0.020-0.040 inches.

23. The textured wipe pad of claim 22, wherein the plurality of beads respectively have diameters in the range of about 0.040-0.60 inches at the base surface.

* * * * *